US00PP10883P

United States Patent [19]

Olesen et al.

[11] Patent Number: Plant 10,883

[45] Date of Patent: May 4, 1995

[54] FLORIBUNDA ROSE PLANT NAMED 'POULTHE'

[75] Inventors: L. Pernille Olesen; Mogens N. Olesen, both of Fredensborg, Denmark

[73] Assignee: Poulsen Roser ApS, Fredensborg, Denmark

[21] Appl. No.: 08/865,462

[22] Filed: May 29, 1997

[51] Int. Cl.[6] ..... A01H 5/00

[52] U.S. Cl. ..... Plt./141

[58] Field of Search ..... Plt./22, 27, 28, Plt./141, 149, 150

[56] References Cited

U.S. PATENT DOCUMENTS

P.P. 9,062 2/1995 Olesen et al. ..... Plt./1

OTHER PUBLICATIONS

UPOU–ROM, 1998/01, Plant Variety Database, GTI Jouve Retrieval Software, Citations for 'POULthe'.

*Primary Examiner*—Howard J. Locker

[57] ABSTRACT

A new floribunda rose plant with mauve colored flowers which has abundant non-fading flowers and very good keepability. The variety successfully propagates from softwood cuttings and is suitable for year round production in commercial glasshouses. This new and distinct variety has shown to be uniform and stable in the resulting generations from asexual propagation.

2 Drawing Sheets

SUMMARY OF THE DISCOVERY

The present discovery constitutes a new and distinct variety of floribunda rose plant which was discovered in the spring of 1990 in a cultivated area. The mutation resulted from a naturally occurring mutation of unknown causation discovered in a controlled planting as a branch of 'POULskov', a patented variety described and illustrated in U.S. Plant Pat. No. 9,062 and issued on Feb. 28, 1995. The new variety is named 'POULthe'.

The rose plant of the present discovery has a unique combination of characteristics which are outstanding in the new variety and which distinguish it from the original rose 'POULskov' as well as all other varieties which we are aware of. For example, the new variety:

1. Has abundant, uniform, mauve flowers and quick reblooming cycle;

2. Attractive long lasting foliage and compact growth.

3. Flowers year-round under glasshouse conditions;

4. Is suitable for production from softwood cuttings in pots;

5. Has durable flowers and foliage which make the variety suitable for distribution in the floral industry.

This combination of qualities is not present in previously available commercial cultivars of this type and distinguish POULthe from all other varieties of which we are aware.

The resulting mutation was evaluated in the spring and summer of 1990 in a controlled environment.

'POULthe' was selected by L. Pernille and Mogens N. Olesen in their rose development program in Fredensborg, Denmark in the summer of 1990.

Asexual reproduction of 'POULthe' by cuttings and traditional budding was first done by L. Pernille and Mogens N. Olesen in August, 1990. This initial and subsequent propagations have demonstrated that the characteristics of 'POULthe' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULthe'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting prickles;

6. Leaves.

Illustrated in SHEET 2 is the variety in a patio planter. This photograph was taken in Fredensborg, Denmark.

DETAILED DESCRIPTION OF THE VARIETY

The following is a detailed description of 'POULthe', as observed in its growth in glasshouses in Fredensborg, Denmark and Half Moon Bay, Calif. and in a field nursery in Applegate, Oreg. Descriptions were made from plants treated with growth regulators normally used in the greenhouse production process. The growth regulator Paclobutrazol was applied at 30 ppm weekly for three weeks beginning at a plant age of 8 weeks. The peduncle lengths mentioned may actually be shorter and the foliage color several shades darker than on untreated specimens. Color references are made using The Royal Horticultural Society (London, England) Colour Chart, 1995, except where common terms of color are used.

For a comparison, the nearest existing rose variety is 'POULskov', a patented variety described and illustrated in U.S. Plant Pat. No. 9,062 and issued on Feb. 28, 1995. Chart 1 details several physical characteristics of applicants' variety and the comparison variety 'POULskov'.

CHART 1

| | 'POULthe' | 'POULskov' |
|---|---|---|
| Color of the flower bud at ¼ opening. | RHS 57 C of the Red-Purple Group | Between RHS 49 C of the Red Group and RHS 55 D of the Red Group |
| Color or upper surface of petal on an open flower | RHS 57 A of the Red-Purple Group | Between RHS 49 D of the Red Group and RHS 56 B of the Red Group |

Parent: Mutation from 'POULskov', U.S. Plant Pat. No. 9,062, dated Feb. 28, 1995.

Classification:

*Botanical.*—*Rosa hybrida.*

*Commercial.*—*Floribunda.*

Flower and Flower Bud

Blooming cycle: Recurrent.

Flower bud:

*Size.*—18–20 mm in length when petals are just beginning to crack open.

*Bud form.*—Ovoid.

*Bud color.*—R.H.S. 57 C of the Red-Purple Color Group at ¼ opening.

*Sepals.*—R.H.S. 143 C of the Green Group. Foliaceous appendages are not generally present. Surfaces of sepals lightly pubescent.

*Peduncle.*—Surface: Smooth with stipitate glands present. Length: 20–25 mm average length. Color: R.H.S. 143 C of the Green Group. Prickles: Few to none.

*Receptacle.*—Surface: Smooth. Glabrous. Shape: Urn shaped. Size: Medium. 9 mm×10 mm. Color: R.H.S. 143 C of the Green Group.

*Borne.*—1–5 flowers per flowering stem.

Flower bloom:

*Diameter.*—Medium. 40–50 mm on average.

*Form.*—Upon opening, pointed to ovoid to globular. Completely open, flat to flattened convex with petals reflexing.

*Petalage.*—Very double. Average range: 55–60 petals. Generally 1–5 petaloids with same coloration as petals. Petaloid size range from 2 mm to 4 mm in width and 6–8 mm, and longer, in length.

*Color.*—Upon opening, the upper surface is R.H.S. 57 A of the Red-Purple Color Group. Upon opening, the reverse side is R.H.S. 57 C of the Red-Purple Color Group. After opening, the upper surface is R.H.S. 57 C of the Red-Purple Color Group. A small petal spot R.H.S. 2 C of the Yellow Color Group exists on the inner side of the petal base. A small petal spot R.H.S. 2 C of the Yellow Color Group exists on the outer side of the petal base.

*Reflex.*—Petals reflex backwards somewhat.

*Variations.*—Certain flower petals can exhibit a white streak.

*Fragrance.*—Light.

*Duration.*—5–6 days as a cut flower and 8–10 days on the plant.

Flowering stem:

*Length.*—On a nursery plant, 35–45 cm.

Reproductive organs:

*Pollen.*—Yellow Group 13B. Average abundance.

*Anthers.*—Size: Small and abundant. Color: Yellow Group 13C.

*Filaments.*—Color: Green-Yellow Group 1C.

*Stigmas*—Located at same to slightly superior position as anthers. Abundant Color: Green-White Group 157A.

*Styles*—Color: Green-white group 157A with limited intonation of Red-purple group 57D. Abundant.

Plant

Plant growth: Vigorous, compact, and bushy to upright. When grown as a 15 cm pot plant, the average height of the plant itself is 24–28 cm and the average width is 22–24 cm. When grown as a nursery plant on its own roots the average plant height is 65–75 cm and the average plant width is 60–70 cm.

Stems:

*Color.*—Young wood: R.H.S. 143 C of the Green Color Group. Older wood: R.H.S. 143 A of the Green Color Group.

*Prickles.*—Incidence: Few to moderate Prickles. Size: Average length: 5–7 mm. Color: Younger prickles yellow-green group 145C. Older prickles red group 36C. Shape: Linear to concave.

*Bark.*—Young wood: Smooth. Older wood: Smooth.

Plant foliage:

*Normal number of leaflets on average leaves.*—5 leaflets, however a portion have 7 leaves, with the innermost being reduced in size.

*Leaf size.*—Medium. 60×80 mm.

*Abundance.*—Average to abundant.

*Color.*—Mature foliage: Upper leaf surface: Medium to dark green. R.H.S. 137 A of the green color group. Lower leaf surface: Light green. R.H.S. 138 B of the green color group. Juvenile foilage: Green group 137B.

Plant leaves and leaflets:

*Stipules.*—Present. 6–8 mm in length. Limited numbers of stipitate glands present. Color: Green Group 137C. Some with intonation of Red Group 39B.

*Petiole.*—Length: 15–20 mm. Color: Green Group 137C. Underneath: Generally without prickles. Rachis: Color: Green Group 137C.

*Edge.*—Serrated.

*Shape.*—Leaflets are somewhat oval to nearly round.

*Leaflets.*—Number: Generally 5.

*Other.*—Semi-glossy to glossy in finish. Thick textured.

Disease resistance: Above average resistance to mildew, rust, and black spot under normal growing conditions in Half Moon Bay, Calif. and Fredensborg, Denmark.

We claim:

1. A new and distinct variety of rose plant of the floribunda class, substantially as herein illustrated and described, as a distinct and novel rose variety due to its abundant mauve flowers with good keepability, attractive long lasting foliage and compact growth, year round flowering under glasshouse conditions, suitability for production from softwood cuttings in pots, durable flowers which make the variety suitable for distribution in the floral and nursery industry.

* * * * *

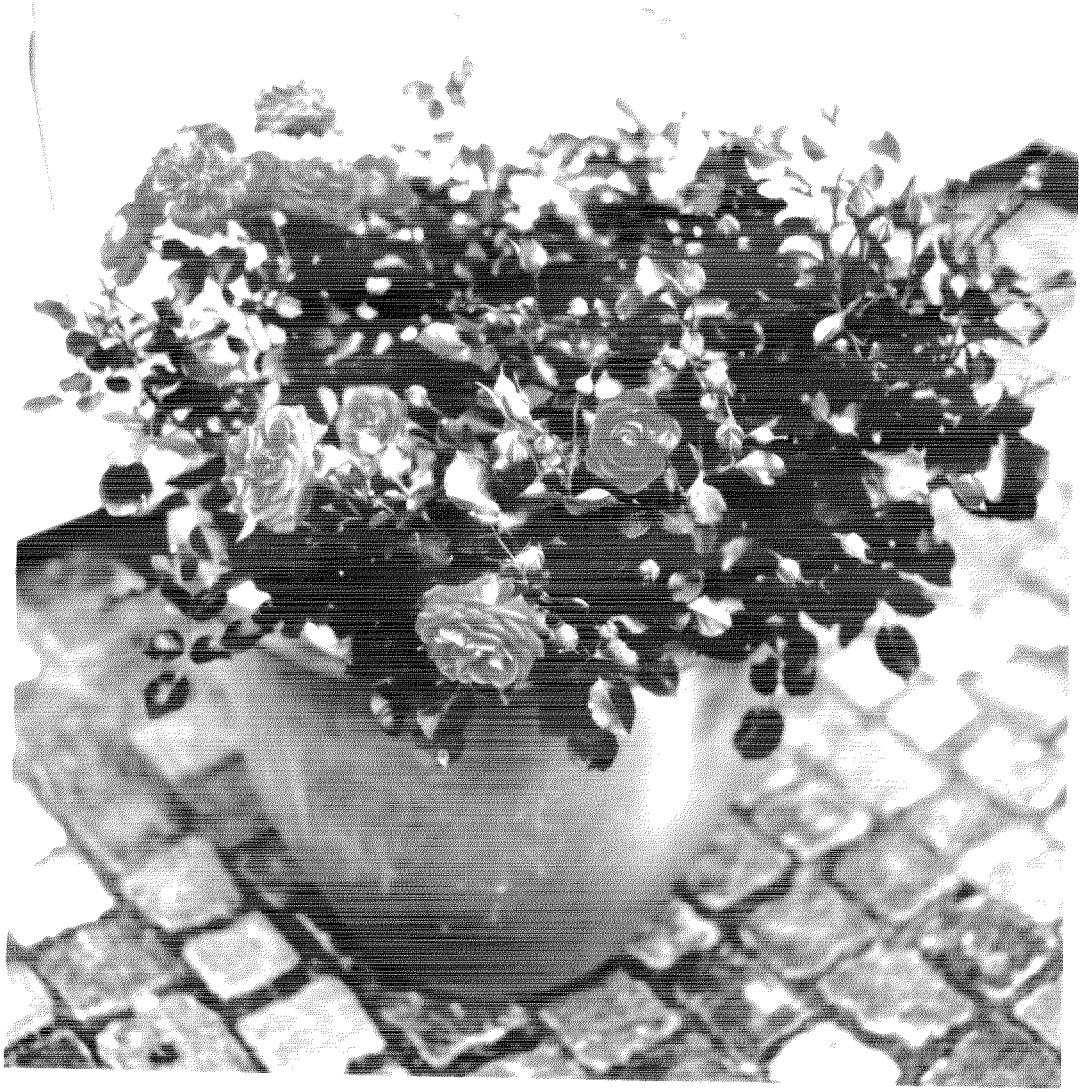

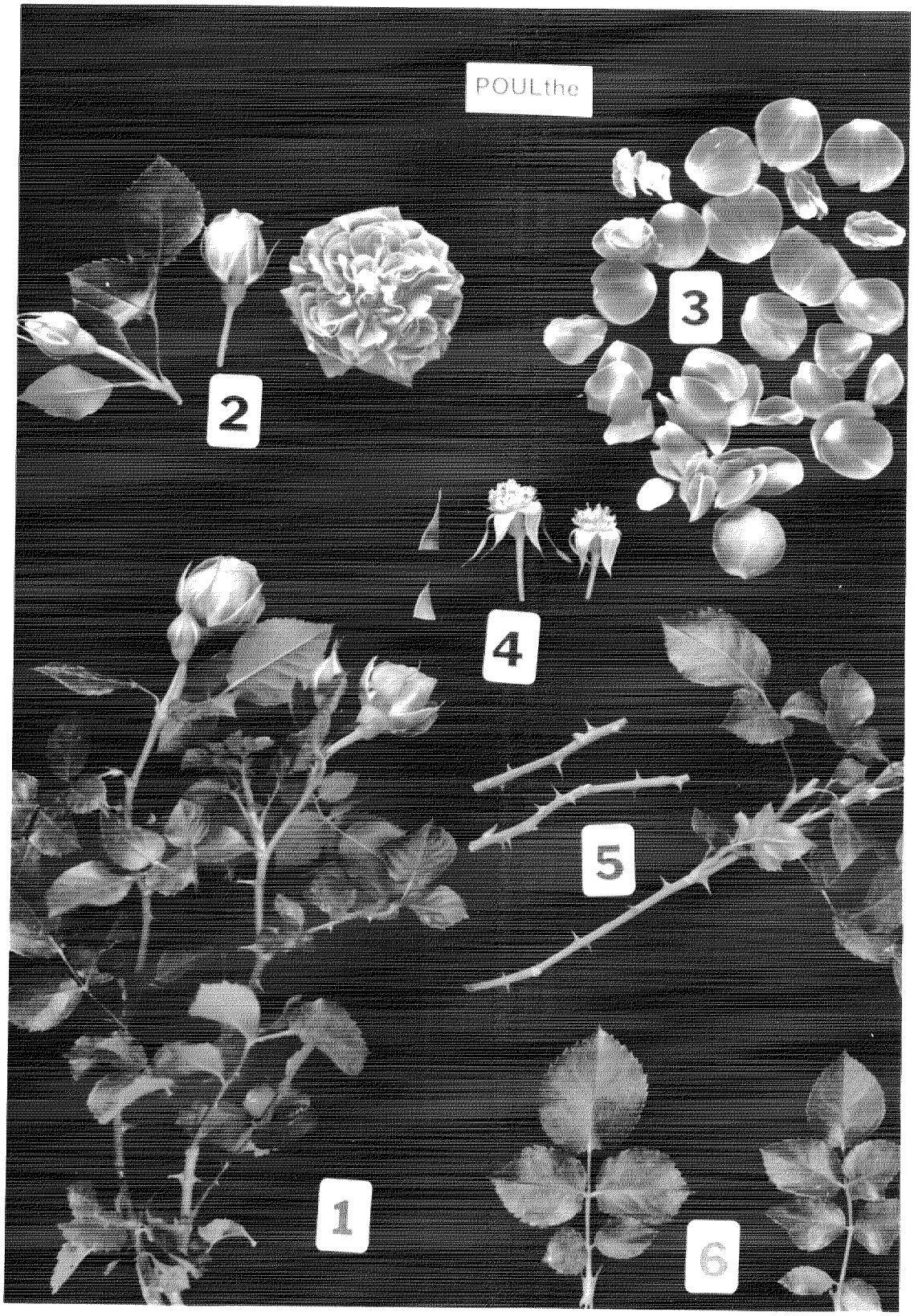
POULthe
2
3
4
5
1
6